US008135730B2

(12) United States Patent
Lim et al.

(10) Patent No.: US 8,135,730 B2
(45) Date of Patent: Mar. 13, 2012

(54) ONTOLOGY-BASED SEARCHING IN DATABASE SYSTEMS

(75) Inventors: Lipyeow Lim, Hawthorne, NY (US); Anastasios Kementsietsidis, New York, NY (US); Min Wang, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 245 days.

(21) Appl. No.: 12/481,009

(22) Filed: Jun. 9, 2009

(65) Prior Publication Data
US 2010/0312779 A1     Dec. 9, 2010

(51) Int. Cl.
G06F 17/30     (2006.01)
(52) U.S. Cl. .......... 707/768; 707/706; 707/758; 706/11; 706/12; 706/45; 706/62
(58) Field of Classification Search .......... None
See application file for complete search history.

(56) References Cited

U.S. PATENT DOCUMENTS

| | | | |
|---|---|---|---|
| 6,038,560 A | 3/2000 | Wical | |
| 7,328,209 B2 | 2/2008 | Das et al. | |
| 7,496,593 B2 * | 2/2009 | Gardner et al. | 1/1 |
| 7,526,425 B2 * | 4/2009 | Marchisio et al. | 704/9 |
| 7,620,542 B2 * | 11/2009 | Sheu et al. | 704/9 |
| 7,630,981 B2 * | 12/2009 | Xu et al. | 1/1 |
| 7,685,118 B2 * | 3/2010 | Zhang | 706/55 |
| 2002/0059289 A1 * | 5/2002 | Wenegrat et al. | 707/102 |
| 2005/0149510 A1 * | 7/2005 | Shafrir | 707/3 |
| 2006/0047632 A1 * | 3/2006 | Zhang | 707/3 |
| 2006/0053151 A1 * | 3/2006 | Gardner et al. | 707/102 |
| 2006/0248458 A1 * | 11/2006 | Li | 715/700 |
| 2007/0106499 A1 * | 5/2007 | Dahlgren et al. | 704/10 |
| 2007/0150458 A1 * | 6/2007 | Chung et al. | 707/3 |
| 2007/0174041 A1 * | 7/2007 | Yeske | 704/3 |
| 2007/0208726 A1 * | 9/2007 | Krishnaprasad et al. | 707/4 |
| 2007/0250493 A1 * | 10/2007 | Peoples et al. | 707/4 |
| 2008/0040308 A1 | 2/2008 | Ranganathan et al. | |
| 2009/0112838 A1 * | 4/2009 | Eggebraaten et al. | 707/5 |
| 2010/0036797 A1 * | 2/2010 | Wong et al. | 706/55 |
| 2011/0004588 A1 * | 1/2011 | Leitersdorf et al. | 707/711 |

OTHER PUBLICATIONS

Das et al, "Supporting Ontology-based Semantic Matching in RDBMS", Proceedings of the 30th VLDB Conference, Canada, 2002.*
Kementsietsidis et al, "Supporting Ontology-based Keyword Search Over Medical Databases" AMIA, 2002.* Ko et al, "Ontology-based Context Modeling and Reasoning for U-Healthcare", IEICE Trans, 2002.*
Wang et al, "Ontology Based Context Modeling and Reasoning using OWL", IEEE, 2004.*
Zhang et al, "Si-SEEKER: Ontology-Based Semantic Search over Databases", Springer-Verlag Berlin Heidelberg, 2006.*
Zhou, Jian, et al., "Minerva: A Scalable OWL Ontology Storage and Inference System," Lecture Notes in Computer Science, Springer Berlin/Heidelberg, ISSN 0302-9743, viol, 4185/2006, The Semantic Web—ASWC 2006, ISBN 978-3-540-38329-1, 2006.

* cited by examiner

Primary Examiner — Hung Le
(74) Attorney, Agent, or Firm — Jose Gutman; Fleit Gibbons Gutman Bongini & Bianco PL

(57) ABSTRACT

A method, information processing system, and computer program storage product retrieve data from a database. A search request is received from a user for a set of data in at least one database. An ontology query over is performed over at least one ontology associated with at least one database resulting in an ontological dataset associated with the search request in response to receiving the search request from the user. The ontological dataset includes at least one of a set of synonyms, a set of hypernyms, and a set of hyponyms, associated with the search request. A data query is performed over data in the at least one database using the ontological dataset in response to performing the ontology query. The set of data is returned to the user based on the data query that has been performed.

17 Claims, 9 Drawing Sheets

| vID | Date | patID | diag |
|-----|----------|-------|------------------------|
| 1 | 20080201 | 3343 | Brain Tumor |
| 7 | 20080205 | 1255 | Neurocytoma |
| 3 | 20080202 | 4555 | Intraventricula Neoplasm |
| 4 | 20080204 | 6565 | Pineoblastoma |
| 6 | 20080101 | 9878 | Pineocytoma |

FIG. 2

| src | rel | tgt |
|---|---|---|
| Brain Neoplasm | hasCode | C9344 |
| Brain Neoplasm | hasHyponym | Intraventricular Brain Neoplasm |
| Brain Neoplasm | hasSynonym | Brain Tumor |
| Brain Neoplasm | hasHyponym | Supratentorial Neoplasm |
| Pineoblastoma | hasSynonym | PNET of Pineal Gland |
| Pineoblastoma | hasSynonym | Pineal PNET |

402 points to the first data row.

FIG. 4

502:
```
SELECT DISTINCT V.* FROM Thesaurus T, Visit V WHERE src IN
   (SELECT src FROM Thesaurus WHERE tgt = 'QTerm' AND rel = 'hasSynonym')
   AND T.rel = 'hasSynonym' AND T.tgt = V.diag
```

504:
```
WITH Traversed (src) AS (
   (SELECT src FROM Thesaurus WHERE tgt = 'QTerm' AND rel = 'hasSynonym')
   UNION ALL
   (SELECT CH.tgt FROM Traversed PR, Thesaurus CH
    WHERE PR.src = CH.src AND CH.rel = 'hasHyponym'))
SELECT DISTINCT V.* FROM Thesaurus T, Visit V WHERE src IN
   (SELECT DISTINCT src FROM Traversed) AND T.rel = 'hasSynonym'
   AND t.tgt = V.diag
```

FIG. 5

| src | tgt |
|---|---|
| Brain Neoplasm | Intraventricular Brain Neoplasm |
| Brain Neoplasm | Supratentorial Neoplasm |

The *Hyponym* relation

| src | tgt |
|---|---|
| Pineoblastoma | PNET of Pineal Gland |
| Pineoblastoma | Pineal PNET |

The *Synonym* relation

```xml
<?xml version="1.0" encoding="UTF-8"?>
<!DOCTYPE terminology SYSTEM "ontylog.dtd">
<terminology ref_by="name" if_exists_action="replace">
...
<conceptDef>
   <name>Pineoblastoma</name>
   <code>C9344</code>
   <id>9344</id>
   <namespace>NCI</namespace>
   <kind>Findings_and_Disorders_Kind</kind>
   <definingConcepts>
      <concept>Embryonal_Neoplasm_of_the_CNS</concept>
      <concept>Malignant_Pineal_Region_Neoplasm</concept>
      <concept>Pineal_Parenchymal_Cell_Neoplasm</concept>
   </definingConcepts>
   ...
   <properties>
      <property>
         <name>Preferred_Name</name>
         <value>Pineoblastoma</value>
      </property>
      <property>
         <name>Synonym</name>
         <value>PNET of Pineal Gland</value>
      </property>
      <property>
         <name>Synonym</name>
         <value>Pineal Gland PNET</value>
      </property>
      ...
   </properties>
</conceptDef>
...
<conceptDef>
   <name>Malignant_Pineal_Region_Neoplasm</name>
   <code>C3573</code>
   ...
</conceptDef>
...
```

FIG. 7

802 {
```
SELECT DISTINCT V.* FROM Visit V WHERE V.diag IN
   (SELECT DISTINCT src FROM XMLTABLE ('db2-fn:xmlcolumn("ORG.DAT")
   /terminology/conceptDef/properties[property/name/text()="Synonym" and
   property/value/text()="QTerm"]/property[name/text()="Synonym"]/value
   COLUMNS syn CHAR(64) PATH'.') AS Temp)
```

804 {
```
WITH Traversed (cls, src) AS (
   (SELECT R.cls, R.syn FROM XMLTABLE ('db2-fn:xmlcolumn("ORG.DAT")
   /terminology/conceptDef/properties[property/name/text()="Synonym" and
   property/value/text()="QTerm"]/property[name/text()="Synonym"]/value
   COLUMNS cls CHAR(64) PATH'./parent::*/parent::*/parent::*/name',
             syn CHAR(64) PATH'.') AS R)
   UNION ALL
   (SELECT CH.cls, CH.syn FROM Traversed PR,
   XMLTABLE ('db2-fn:xmlcolumn("ORG.DAT")
   /terminology/conceptDef/definingConcepts/concept[,/text()=$parent]/
   parent::*/parent::*/properties/property[name/text()="Synonym"]/value'
   PASSING PARENT.cls AS "parent"
   COLUMNS cls CHAR(64) PATH,/parent::*/parent::*/parent::*/name',
             syn CHAR(64) PATH'.') AS CH))
SELECT DISTINCT V.* FROM Visit AS V
WHERE V.diag IN (SELECT src FROM Traversed)
```

FIG. 8

902 {
```
WITH Traversed (elem, attr) AS (
   (SELECT X.elem, X.attr FROM Synonym S,
      XMLTABLE ('db2-fn:xmlcolumn("XR.DAT")//.[fn:name(.)=$start]//.'
      PASSING BY REF S.src AS "start"
      COLUMNS elem CHAR(64) PATH'fn:name(.)',
         attr CHAR(64) PATH 'if (fn:exists(.[@cp])) then./@cp else "F"') AS X)
   WHERE S.tgt = QTerm
   UNION ALL
   (SELECT X.elem, X attr FROM
      (SELECT * FROM TRAVERSED T WHERE T.attr='T') AS T1
      XMLTABLE ('db2-fn:xmlcolumn("XR.DAT")
      //*[fn.name(.) = $n and @cp="MR"]//.'
      PASSING T1.elem AS "n"
      COLUMNS elem CHAR(64) PATH'fn:name(.)',
         attr CHAR(64) PATH 'if (fn:exists(.[@cp])) then./@cp else "F"') AS X)
SELECT DISTINCT V.* FROM Visit V WHERE V.diag IN
   (SELECT DISTINCT S.tgt FROM Synonym S, Traversed T)
   WHERE S.src = T.elem
```

FIG. 9

| ID | Date | Patient | Daignosis | Annotation |
|---|---|---|---|---|
| 1 | 20080201 | 3343 | Brain Tumor | Brain Tumor |
| 7 | 20080205 | 1255 | Neurocytoma | |
| 3 | 20080202 | 4555 | Intraventricula Neoplasm | |
| 4 | 20080204 | 6565 | Pineoblastoma | |
| 6 | 20080101 | 9878 | Pineocytoma | |

ONTOLOGY-BASED SEARCHING IN DATABASE SYSTEMS

FIELD OF THE INVENTION

The present invention generally relates to the field of database systems, and more particularly relates to searching database systems using ontology-based searches.

BACKGROUND OF THE INVENTION

Databases often contain different entries for similar data sets, which often results in relevant data not being returned for a query. Take for example a medical records database, where the proliferation of medical terms is a major obstacle in the sharing of medical information among different shareholders (e.g., hospitals, clinicians, pharmaceutical companies etc.). Different clinicians within a hospital often use distinct terms to refer to the same diagnosis, while symptoms are often recorded to a patient's record in varying levels of granularity. For example, one clinician might describe a patient diagnosis using the term "Pineoblastoma", while another might use the (synonym) term "PNET of Pineal Gland". Therefore, a query for records comprising "Pineoblastoma" usually only returns the record including "Pineoblastoma" and not the record including "PNET of Pineal Gland". Also, a generic term such as "Brain Neoplasm" might be recorded in a record instead of the more specific "Pineoblastoma" (where the latter term is said to be a hyponymn of the former). Therefore, a query for records comprising "Pineoblastoma" usually would not return the record comprising "Brain Neoplasm" even though the term "Brain Neoplasm" includes "Pineoblastoma".

As can be seen data sets in a database can be represented using different terms, which usually results in a query only returning records that exactly match the query terms even though additional records are relevant to the query. This incomplete query result does not provide all relevant information to the user and can cause critical information to be missed.

SUMMARY OF THE INVENTION

In one embodiment, a method for retrieving data from a database is disclosed. The method comprises receiving a search request from a user for a set of data in at least one database. An ontology query is performed over at least one ontology associated with at least one database resulting in an ontological dataset associated with the search request in response to receiving the search request from the user. The ontological dataset comprises of zero or more synonyms and/or zero or more hypernyms and/or zero or more hyponyms associated with the search request. A data query is performed over data in the at least one database using the union of the ontological dataset with the original search keywords in the original search request. The set of data is returned to the user based on the data query that has been performed.

In another embodiment, an information processing system for retrieving data from a database is disclosed. The information processing system includes a memory and a processor communicatively coupled to the memory. A database manager is communicatively coupled to the memory and the processor. The database manager is adapted to receive, from a user, a search request for a set of data in at least one database. An ontology query over is performed over at least one ontology associated with at least one database resulting in an ontological dataset associated with the search request in response to receiving the search request from the user. The ontological dataset includes at least zero or more synonyms and/or zero or more hypernyms and/or zero or more hyponyms associated with the search request. A data query is performed over data in the at least one database using the union of the ontological dataset with the original search keywords in the original search request. The set of data is returned to the user based on the data query that has been performed.

In yet another embodiment, a computer program storage product for retrieving data from a database is disclosed. The computer program storage product comprises instructions for receiving a search request is from a user for a set of data in at least one database. An ontology query over is performed over at least one ontology associated with at least one database resulting in an ontological dataset associated with the search request in response to receiving the search request from the user. The ontological dataset comprises of zero or more synonyms and/or zero or more hypernyms and/or zero or more hyponyms associated with the search request. A data query is performed over data in the at least one database using the union of the ontological dataset with the original search keywords in the original search request. The set of data is returned to the user based on the data query that has been performed.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIG. 2 shows one example of a database record according to one embodiment of the present invention;

FIG. 4 shows an example of a tuples resulting from processing an ontology based on a user search request according to one embodiment of the present invention;

FIG. 5 shows examples of an ontology query according to one embodiment of the present invention;

FIG. 6 shows synonym and hyponym relations according to one embodiment of the present invention;

FIG. 7 shows an excerpt from the NCI Thesaurus;

FIGS. 8-9 shows additional ontology queries according to one embodiment of the present invention;

FIG. 10 shows another example of a database record with a dynamically added annotation column according to one embodiment of the present invention;

DETAILED DESCRIPTION

As required, detailed embodiments of the present invention are disclosed herein; however, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure and function. Further, the terms and phrases used herein are not intended to be limiting; but rather, to provide an understandable description of the invention.

The terms "a" or "an", as used herein, are defined as one or more than one. The term "set", as used herein, comprises zero or more elements. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Operating Environment

Figure 1:
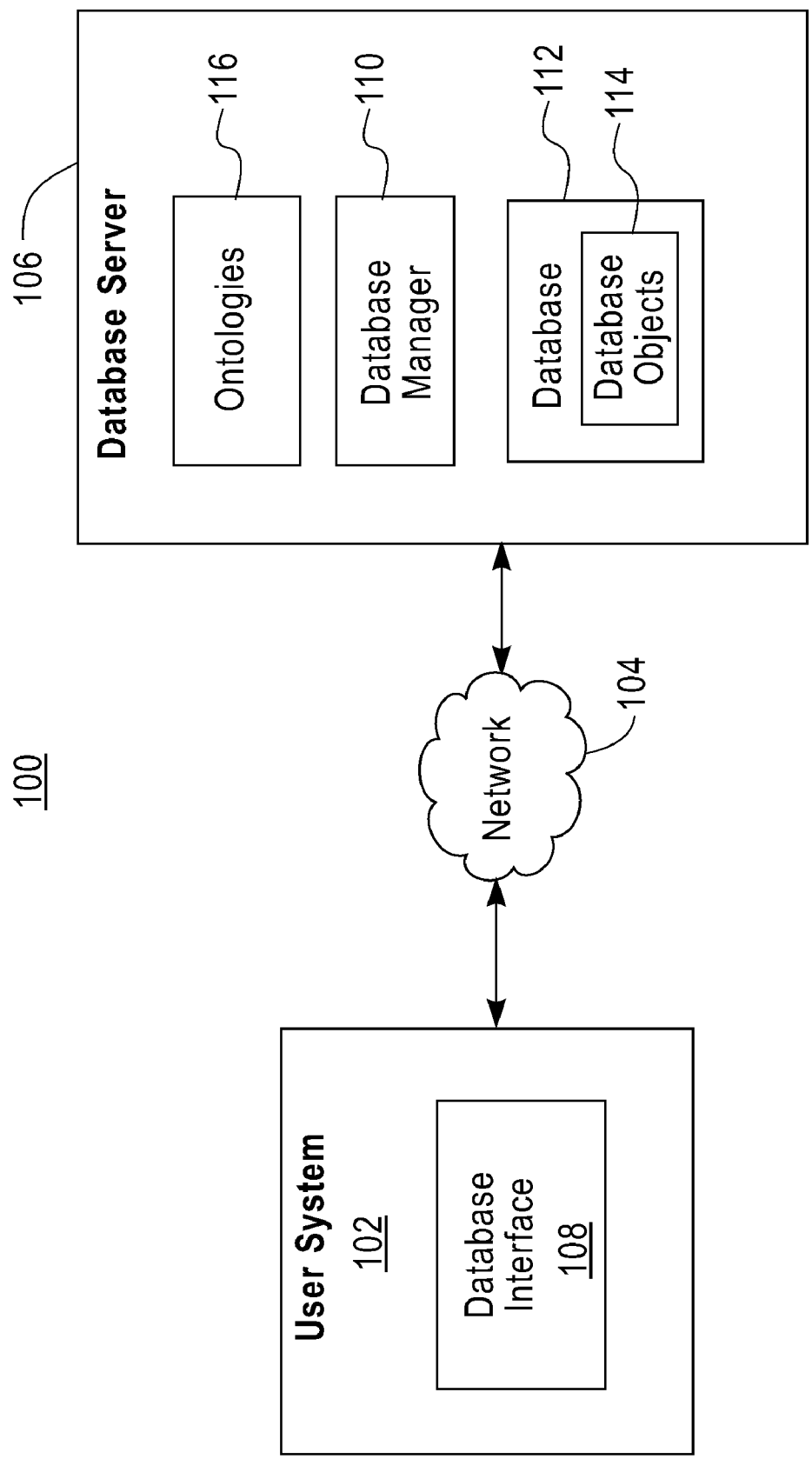
FIG. 1 is a block diagram illustrating one example of an operating environment according to one embodiment of the present invention.

According to one embodiment of the present invention, as shown in FIG. 1, a system 100 for performing ontology-based searches of database systems is shown. In one embodiment, the system 100 includes one or more user information processing systems 102, a network 104, and one or more database servers 106. The network 104, in one embodiment, is a wide area network, local area network, wireless network, or the like. The user system 102 includes a database interface 108 for interacting with the database server 106. For example, the database interface 108 allows a user to submit one or more search requests to the database server 106 to obtain data from one or more databases 112 associated with the database server 106. The database interface 108 can also provide a display interface to the user to view the search request results.

The database server 106 includes a database manager 110 that manages one or more databases 112 comprising database objects 114. The database manager 110 performs one or more actions on the databases 112 in response to instructions received from a user. For example, the database manager 110 retrieves information from the databases 112 in response to a search request received from the user. In one embodiment, the one or more databases 112 are relational databases organizing the data 114 in one or more tables. However, the various embodiments of the present invention are not limited to relational databases. For example, the various embodiments of the present invention are also applicable to mark-up language databases, hybrid relational-XML databases, and the like.

The database server 106 also includes one or more ontologies 116, which are formals representations of one or more concepts in a given domain and the relationship between those concepts. It should be noted that the databases 112 and the ontologies 116 can reside within the database server 106 and/or on one or more different servers. The ontologies 116 can be stored using either relational triple or XML. Columns of the database tables can be associated with one or more ontologies 116. The database manager 110, in one embodiment, uses the ontologies 116 to perform an ontology based database search when retrieving data from the databases 112 in response to a user search request. The database manager 110 and the ontology-based database searches are discussed in greater detail below.

Ontology Based Database Searches

The following is a more detailed discussion on ontologies and using ontologies when performing a database search. It should be noted that although the following discussion uses medical records as the database records being searched and the National Cancer Institute Thesaurus as the basis for an ontology the various embodiments of the present invention are not limited to these examples.

As discussed above, databases often contain different entries for similar data sets, which often results in relevant data not being returned for a query. Therefore, ontologies can be applied to databases to help ensure that all relevant data for a query is returned. However, conventional database systems usually do not provide an efficient way to utilize ontologies. For example, in the medical industry, electronic medical records ("EMRs") are usually stored for efficiency in relational databases and one would expect that it is straightforward to bridge the gap between the term ontology and the EMR database so as to use the former to retrieve records from the latter. The following example illustrates that unfortunately this is not the case.

Consider an EMR database, like the one shown FIG. 2, which stores hospital patient visits. For each visit, it stores its identifier "vid" 202, the "date" 204, patient identifier "patID" 206, and a diagnosis "diag" 208 using terms from the National Cancer Institute ("NCI") NCI Thesaurus. Assume that a clinician wants to retrieve all the patients with a diagnosis of brain tumor. To search for such records, the clinician must (a) access the NCI thesaurus; (b) make a note of all the NCI synonym terms referring to brain tumor (in this case, there are 7 synonyms); and (c) use these terms to issue a query over the relational database to retrieve all relevant records (in this case, the records with vid's 1 and 3).

This approach is clearly inefficient since it requires a great deal of manual effort. The situation is even worse if the clinician also considers the hyponyms (i.e., a word whose semantic range is included within that of another word) of brain tumor in order to retrieve all the patient records whose diagnosis refers to special cases of brain tumor (e.g., terms like "Pineoblastoma" or "Thalamic Neoplasm"). Currently, there are over 230 such terms in NCI. It is practically impossible for the clinician to extract all this information manually from the NCI thesaurus in order to search for the appropriate records. Some level of automation is obviously required here.

In this setting and other settings, it would be beneficial if the clinician were provided with a simple interface. Then, the clinician would only need to perform the following steps: (a) indicate a medical term QTerm; and (b) specify whether, or not, the search should also consider the hyponyms of QTerm (synonyms of QTerm and all of its hyponyms are considered, by default). The various embodiments of the present invention provide this efficient and advantageous searching method. Stated differently, the various embodiments of the present invention enable ontology-based keyword searches over a relational record database.

For example (and as will be discussed in greater detail below), given the input term QTerm, the database manager 110 automatically performs the following steps (i) it looks for QTerm in one or more ontologies 116 and, depending on whether the user has indicated hyponyms are to be used, the database manager also collects the hyponyms of QTerm; and (ii) it uses the collected terms to retrieve the database records. This ontology-based database searching method is discussed in greater detail below.

In one embodiment, an ontology 116 is associated with one or more databases 112 or database records. This can include either loading an ontology 116 into a database system or pointing a database system/record to an ontology 116 stored on a remote system. In one embodiment, the database records such as EMRs are stored in a relational database, in a relation like the one in shown in FIG. 2. In practice, EMRs are often stored as relational records for efficient processing. However, the various embodiments of the present invention are equally applicable to database records stored in an XML format such as those using the HL7 CDA or CCR information models (See, for example, J. M. Ferranti, R. C. Musser, K. Kawamoto, and W. E. Hammond. The clinical document architecture and the continuity of care record: A critical analysis. *Journal of the American Medical Informatics Association*, 13(3):245-252, June 2006, which is hereby incorporated by reference in its entirety). Unlike database records, ontologies are hierarchical in nature with the terms in the hierarchy often forming a directed acyclic graph ("DAG"). Therefore, ontologies can be represented using both XML and the relational model.

Figure 3:
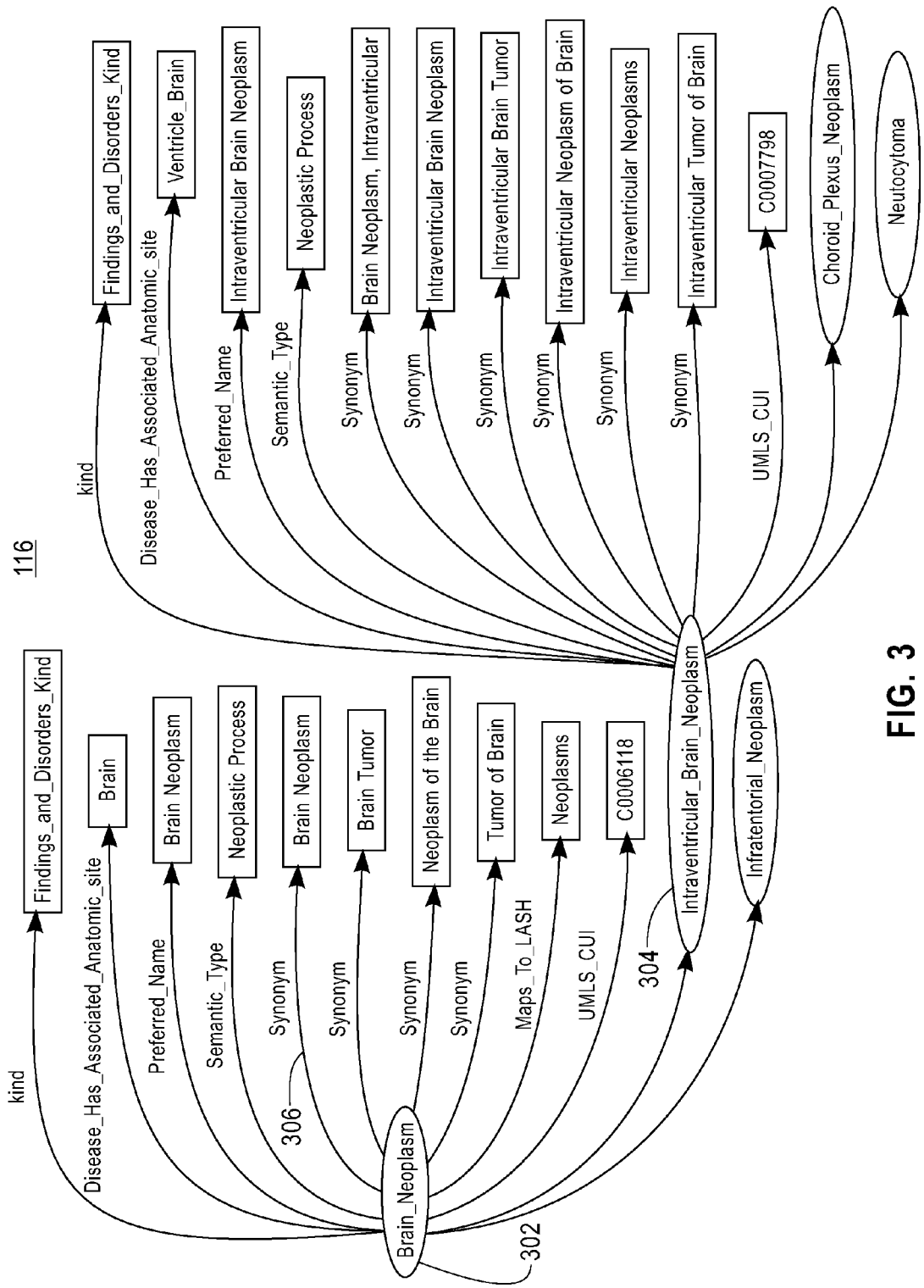
FIG. 3 shows one example of an ontology according to one embodiment of the present invention.

FIG. 3 shows one example of an ontology 116 that has been created using the NCI Thesaurus. In particular, FIG. 3 show shows an ontology 116 represented as a DAG. FIG. 3 shows a root node 302 entitled "Brain Neoplasm". Each child node is a synonym of "Brain Neoplasm". For example, the child node 304 "Intraventricular Brain Neoplasm" is synonym of "Brain Neoplasm". "Intraventricular Brain Neoplasm" is a hypernym of "Intraventricular Brain Neoplasm" and "Intraventricular Brain Neoplasm" is a hyponym of "Brain Neoplasm". The DAG format comprises dimension as specified by a "property" edge type 306 (e.g., "synonym") and a DAG-forming edge type (e.g., "is-a"). These edge types are used by the database manager 110 when processing the ontology.

As discussed above, a user submits a search request to the database manager 110. The search request comprises set of keywords, set of dimension specifications, a set of ordering specifications, and/or a set of aggregation specifications. The keywords are used by the database manager 110 to search the ontology 116 and the database 112 to retrieve information. The dimension specifications indicate whether the database manager 110 is to use hyponyms and/or hypemyms when using the keywords to process the ontology 116. The ordering and aggregation specifications indicate to the user how the results are to be ordered and grouped.

Once the database manager 110 receives the user search request it translates the search request into a database language (e.g., SQL, SQL/XML, XQuery, and the like) in order to perform a query on the ontology 116 and the database 112. For example, Table 1 below shows how a user search request for "Brain Tumor" can be translated into a database query language.

TABLE 1

```
WITH Traversed (src, depth, path) AS
(
    SELECT src, 1, CAST( src AS VARCHAR(60) )
    FROM Synonym
    WHERE tgt = 'Brain Tumor'
    UNION ALL
    SELECT Child.tgt, Parent.depth+1,
        CASE WHEN Parent.depth<2 THEN
        CONCAT(CONCAT(Parent.path,'/'),Child.tgt)
            ELSE Parent.path
        END
    FROM Traversed AS Parent, Subclass AS Child
    WHERE Parent.src = Child.src
)
SELECT V.*, T.path
FROM Visit V, Synonym S, Traversed T
WHERE S.src=T.src
    AND V.diagnosis = S.tgt
ORDER BY T.path
```

As discussed above the user can indicate or annotate the search request with dimension specifications. If a user does not indicate any dimension specification the database manager 110 can select a default dimension such as hyponym. If the user does not specify any of the other specifications such as group the database manager 110 can also select a default specification such as children (e.g., a grouping specification). As Table 1 shows, the user search request is translated into a query that searches for a target "Brain Tumor" and its synonyms with a depth of its child in the ontology 116.

The following are various embodiments for processing an ontology 116 such as the ontology shown in FIG. 3 with respect to a search request comprising search keywords received from a user and a database. One embodiment uses a resource description framework ("RDF") relational method. In this embodiment, a single relation (which is arbitrarily designated as Thesaurus for illustration purposes only) is used to encode the entire ontology 116.

FIG. 4 shows some of the tuples in the Thesaurus relation storing the RDF-like representation of the NCI Thesaurus. Each triplet in the relation such as a first triplet 402 comprising "Brain Neoplasm, hasCode, C9344" determines a relationship rel between a subject src (source) and an object tgt (target). Of particular interest are the relationships "hasSynonym" and "hasHyponym". The former is used to identify the synonyms of a terms. The latter is used to identify the hyponym terms of a term. Notice that each tuple records in the tgt attribute only one of the immediate hyponyms of the term stored in src.

Therefore, a recursive query is used to identify and retrieve all the hyponyms, i.e., the hyponyms of the hyponyms, and then their hyponyms, and so on and so forth. FIG. 5 shows queries Q1 502 and Q2 504, where the former query only retrieves patient records with a diagnosis that is synonymous to QTerm while the latter query also (recursively) considers the hyponyms.

Another embodiment utilizes a native relational method to process ontologies. Unlike the RDF relational method where only a single relation is used, here multiple relations are created to encode the ontology 116. Intuitively, a separate relation is generated for each type of relationship between the terms of the ontology 116. FIG. 6 shows the distinct relations 602, 604 used to represent the synonym and hyponym relationships in the NCI Thesaurus. The corresponding queries Q3 and Q4 are quite similar to those for the RDF relational method discussed above.

Yet another embodiment, utilizes an original XML ontology method to process ontologies. The method considered here assumes that a domain expert provides an XML representation of the ontology. This is indeed the case for the NCI Thesaurus (which is the ontology example being used here). This method requires the least effort since the only thing required is to download the ontology (for example, the NCI Thesaurus), and insert it as is in a database. FIG. 7 shows a fragment 700 of the NCI Thesaurus XML and FIG. 8 shows corresponding queries Q5 802 and Q6 804 for retrieving patient records with a diagnosis that is a synonym or hyponym to QTerm, respectively.

A further embodiment utilizes a hybrid XML fragmentation method. In this embodiment, the original XML ontology tree is decomposed into a number of XML fragments (subtrees). One fragment is created for each term in the ontology. For example, for the NCI Thesaurus XML in FIG. 7, each conceptDef element is extracted as a fragment and stored in a separate tuple (there are approximately 64000 conceptDef elements and hence that many tuples). The intuition is that in the majority of cases, only a part of the tree needs to be accessed to execute a query and therefore it is not necessary to always process the whole tree.

By splitting the ontology tree, only the fragment trees corresponding to terms that are relevant to a query are accessed. Furthermore, by storing each fragment as a tuple in a relation this embodiment is taking advantage of relational database technology (like indexes) to reduce query processing times. The structure of the corresponding queries, Q7 and Q8, are quite similar to those of the original XML ontology method discussed above and are not shown.

Another embodiment uses a hybrid XML tree method to process ontologies. This embodiment starts from the original XML ontology tree and creates (i) a single XML tree to encode the hyponym relationship between terms; and (ii) a synonym relation like the one shown in FIG. 6 to store the synonym relationship between terms. Intuitively, in this embodiment, for each relationship the model of representation is chosen that is more appropriate for it. So, the hyponym relationship which is inherently hierarchical is naturally represented as an XML tree, while the synonym relationship is represented as a relation of synonym term pairs. To retrieve patient records whose diagnosis is synonymous to QTerm, the same query for the native relational method is used. For hyponyms, Q9 902 in FIG. 9 is used.

It should be noted that the processing of an ontology 116 can be performed offline and/or online. For example, an ontology can be applied to database records to obtain all synonyms, hyponyms, and hypemyms of each record entry prior to receiving a user search request. In this embodiment, the keywords in the user search request are compared against the results of previously applying the ontology to the database. However, in another embodiment, the processing of the ontology 116 with respect to the database records can be performed once the user search request is received by the database manager 110.

Once the database manager 110 receives a search request from a user (e.g., the QTerm discussed above) the database manager 110, extracts the keywords from the search request, translates the search request into a database query, and processes the ontology 116 as discussed above. The database manager 110 uses the results of the ontology processing to search the database 112. For example, a user may have transmitted a search request for tuples with the keyword "Brain Tumor". The database manager 110 also analyzes the keywords for search direction annotations. Stated differently, for each keyword or phrase a user can indicate a search direction, which indicates to the database manager 110 whether hyponyms and/or hypernyms of the keywords are to be searched for as well. For example, assume that keyword is "Brain Tumor", a user can indicate whether a hyponym (e.g., Intraventricula Neoplasm) of "Brain Tumor" is to be searched for and/or a hypernym (e.g., Tumor) is to be searched for in addition to the specific keyword of "Brain Tumor".

The results of the ontology search reveal the additional terms (e.g., synonyms, hyponyms, and hypernyms such as Intraventricula Neoplasm and Tumor) that the database manager 110 is to search for in addition to the keywords in the search request. This is advantageous because a conventional search will merely return records matching "Brain Tumor". Therefore, only record 1 in FIG. 2 will be returned even though records 2-5 are all types of a brain tumor.

When the database manager 110 performs the search on the database 110 using the results from the ontology processing, not only are the records matching "Brain Tumor" returned but so are the records matching the terms identified from the ontology search. For example, if the ontology search for "Brain Tumor" resulted in the following terms being identified: "Neurocytoma", "Intraventricula Neoplasm", "Pineoblastoma", and "Pineocytoma", the database manager 110 searches the database for records matching not only "Brain Tumor" but "Neurocytoma", "Intraventricula Neoplasm", "Pineoblastoma", and "Pineocytoma" as well, which results in all of the records shown in FIG. 2 being returned.

In addition, the database manager 110 can dynamically add a column to the database search results based on the grouping specification indicated by the user in the search request. For example, FIG. 10 shows the records that have been returned using an ontology based search. In this example, the user has specified that the results are to be grouped by grandchildren. Therefore, the database manager 110 has dynamically added at least one additional column 1002 to the results that gives a level of abstraction to the user. For example, the user requested a search for the term "Brain Tumor". The database manager 110 using the ontologies 116 identified records down to the grand-child level of "Brain Tumor" in the ontology 116, wherein "Nuerocytoma", "Pineoblastoma", and "Pineocytoma" are grandchildren of "Brain Tumor". The database manager 110 dynamically generates the new column 1002 based on the ontology 116 to indicate to the user what a higher level of the diagnosis is. For example, the annotation column 1002 indicates that "Pineocytoma" is a type or "Supratentorial Neoplasm". FIG. 10 also shows that the database manager 110 has grouped the records by their annotation type.

As can be seen from the above discussion, the various embodiments of the present invention return more useful and complete results to the user by performing an ontology based database search. With the above embodiments an ontology can be loaded into the database system. A user is then able to use the ontology to query database records. The user is only required to input a search term(s) and an indication of whether the hyponyms should also be considered while retrieving records (although a default direction selection can be selected by the database manager 110). A database query on both the ontology and the records table is then executed and the results returned to the user.

Operational Flow For Performing An Ontology Based Database Search

Figure 11:
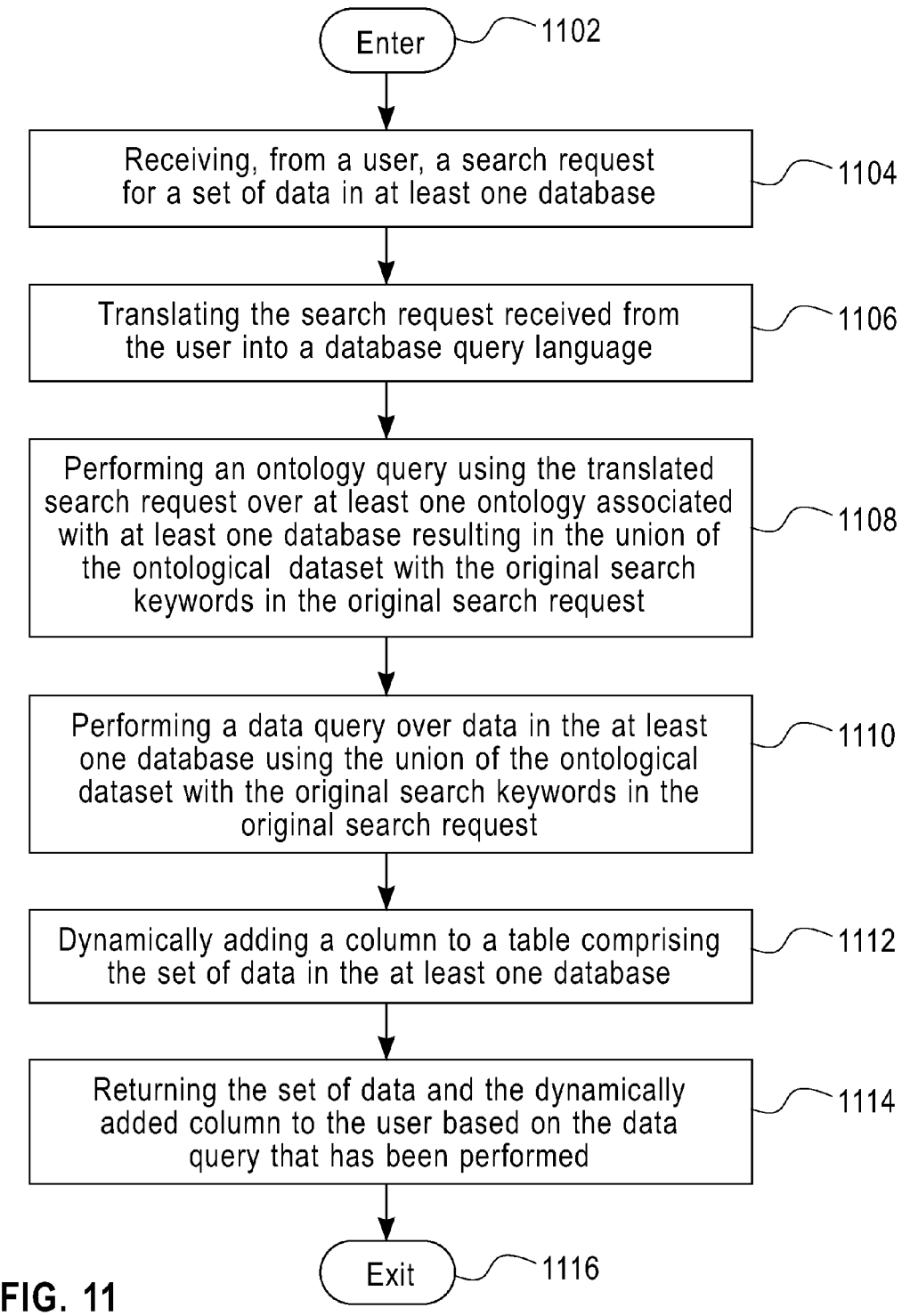
FIG. 11 is an operational flow diagram illustrating one process for performing an ontology based database search.

FIG. 11 is an operational flow diagram illustrating one example of performing an ontology based search on a database. The operational flow diagram of FIG. 11 begins at step 1102 and flows directly into step 1104. The database manager 110, at step 1104, receives a search request for a set of data in at least one database 112 from a user. The database manager 110, at step 1106, translates the user search request into a database language query. The database manager 110, at step 1108, performs an ontology query using the translated search request over at least one ontology 116. This results in a union of the ontological dataset with the original search keywords in the original search request associated with the search request. The database manager 110, at step 1110, performs a data query over data in the at least one database 112. The database manager 110, at step 1112, dynamically adds a column to a table comprising the set of data in the at least one database 112. The database manager 110, at step 1114, returns the set of data including the added column to the user based on the data query that has been performed. The control flow then exits at step 1116.

Information Processing System

Figure 12:
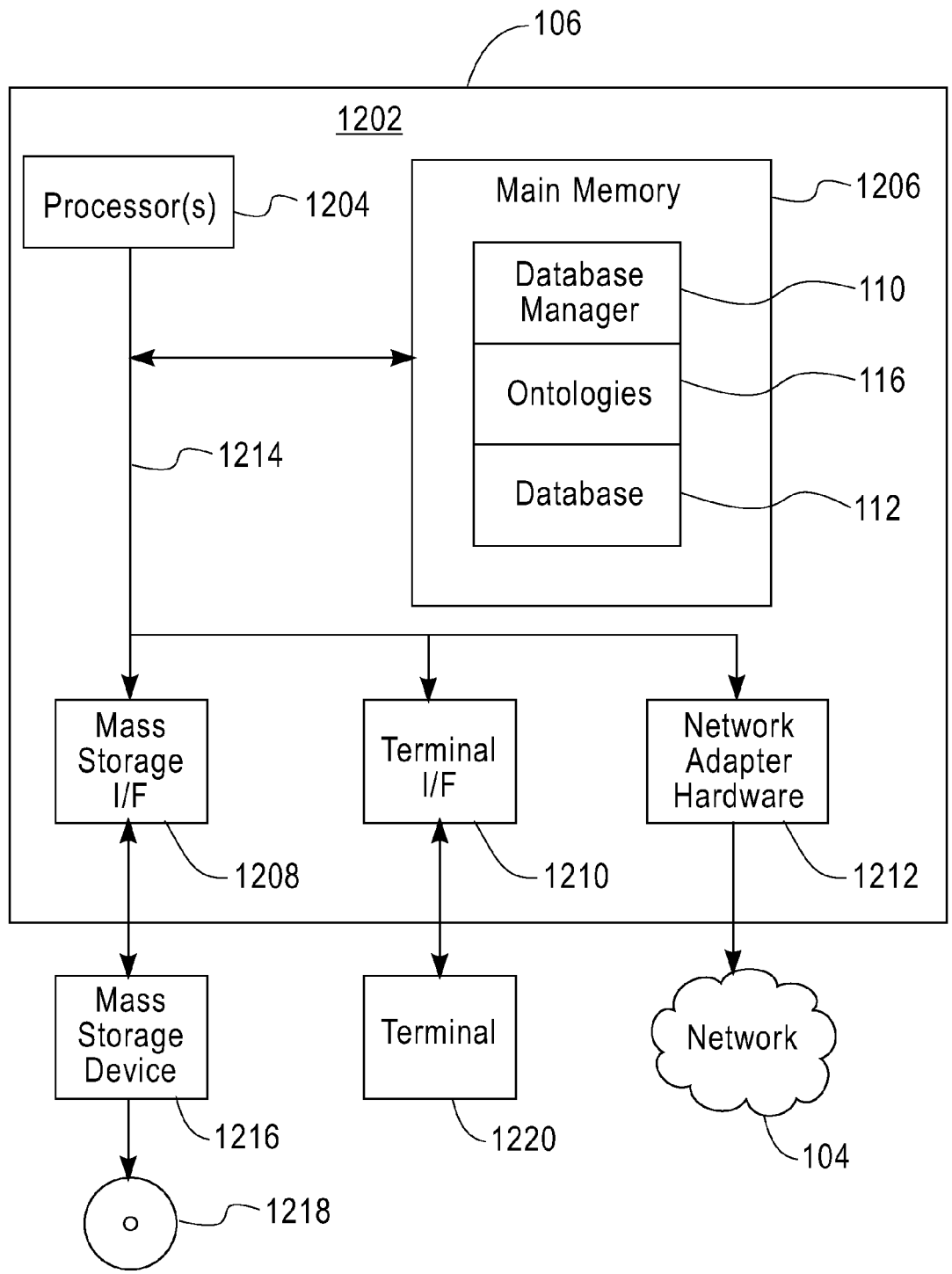
FIG. 12 is a block diagram illustrating a more detailed view of an information processing system according to one embodiment of the present invention.

FIG. 12 is a block diagram illustrating a more detailed view of the information processing system 106 according to one embodiment of the present invention. The information processing system 106 is based upon a suitably configured processing system adapted to implement the exemplary embodiment of the present invention. Any suitably configured processing system is similarly able to be used as the information processing system 106 by embodiments of the present invention such as an information processing system residing in the computing environment of FIG. 1, a personal computer, workstation, or the like.

The information processing system 106 includes a computer 1202. The computer 1202 has a processor(s) 1204 that is connected to a main memory 1206, mass storage interface 1208, terminal interface 1210, and network adapter hardware 1212. A system bus 1214 interconnects these system components. The mass storage interface 1208 is used to connect mass storage devices, such as data storage device 1216, to the information processing system 106. One specific type of data storage device is an optical drive such as a CD/DVD drive, which may be used to store data to and read data from a computer readable medium or storage product such as (but not limited to) a CD/DVD 1218. Another type of data storage device is a data storage device configured to support, for example, NTFS type file system operations.

The main memory 1206, in one embodiment, comprises the database manager 110 and in one embodiment the ontologies 116 and/or the database(s) 112. Although illustrated as concurrently resident in the main memory 206, it is clear that respective components of the main memory 1206 are not required to be completely resident in the main memory 206 at all times or even at the same time. In one embodiment, the information processing system 106 utilizes conventional virtual addressing mechanisms to allow programs to behave as if they have access to a large, single storage entity, referred to herein as a computer system memory, instead of access to multiple, smaller storage entities such as the main memory 1206 and data storage device 1216. Note that the term "computer system memory" is used herein to generically refer to the entire virtual memory of the information processing system 106.

Although only one CPU 1204 is illustrated for computer 1202, computer systems with multiple CPUs can be used equally effectively. Embodiments of the present invention further incorporate interfaces that each includes separate, fully programmed microprocessors that are used to off-load processing from the CPU 1204. Terminal interface 1210 is used to directly connect one or more terminals 1220 to computer 1202 to provide a user interface to the computer 1202. These terminals 1220, which are able to be non-intelligent or fully programmable workstations, are used to allow system administrators and users to communicate with the information processing system 106. The terminal 1220 is also able to consist of user interface and peripheral devices that are connected to computer 1202 and controlled by terminal interface hardware included in the terminal I/F 1210 that includes video adapters and interfaces for keyboards, pointing devices, and the like.

An operating system (not shown) included in the main memory is a suitable multitasking operating system such as the Linux, UNIX, Windows XP, and Windows Server 2003 operating system. Embodiments of the present invention are able to use any other suitable operating system. Some embodiments of the present invention utilize architectures, such as an object oriented framework mechanism, that allows instructions of the components of operating system (not shown) to be executed on any processor located within the information processing system 106. The network adapter hardware 1212 is used to provide an interface to a network 104. Embodiments of the present invention are able to be adapted to work with any data communications connections including present day analog and/or digital techniques or via a future networking mechanism.

Although the exemplary embodiments of the present invention are described in the context of a fully functional computer system, those skilled in the art will appreciate that embodiments are capable of being distributed as a program product via CD or DVD, e.g. CD 1218, CD ROM, or other form of recordable media, or via any type of electronic transmission mechanism.

Non-Limiting Examples

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A method of retrieving data from a database, the method comprising:

receiving, from a user, a search request comprising search keywords for a set of data in at least one database;

performing, in response to receiving the search request from the user, an ontology query over at least one ontology associated with at least one database resulting in an ontological dataset associated with the search request, wherein the ontological dataset comprises at least one of a set of synonyms, a set of hypernyms, and a set of hyponyms associated with the search request;

performing, in response to performing the ontology query, a data query over data in the at least one database using a union of the ontological dataset with the search keywords in the search request, wherein performing the data query further comprises:

searching for a first set of data records associated with the search keywords; and searching for a second set of data records associated with the ontological dataset: and returning the set of data to the user based on searching for the first set of data records and the second set of data records, wherein returning the set of data to the user further comprises: dynamically adding a column to a table comprising the set of data in the at least one database, wherein each row in the column that has been added comprises a grouping annotation associated with a corresponding data entry in the set of data.

2. The method of claim 1, wherein the at least one database is a relational database.

3. The method of claim 1, wherein the search request received from the user comprises at least one of:

a set of search keywords;

a set of dimension specifications for at least one search keyword in the set of search keywords indicating whether the ontology query is to consider at least one of synonyms, hypernyms, and hyponyms in the at least one ontology associated with the at least one search keyword; and an aggregation specification indicating at least one aggregation type for aggregating the at least one of synonyms, hypernyms, and hyponyms, in the at least one ontology for the at least one search keyword.

4. The method of claim 3, wherein the set of dimension specifications for at least one search keyword in the set of search keywords includes an ontological relationship defined in the ontology that is other than a default synonym, hypernym, or hyponym.

5. The method of claim 1, further comprising:

storing the at least one ontology into the at least one database prior to performing the ontology query.

6. The method of claim 1, further comprising:

translating the search request received from the user into a database query language, wherein the ontology query and the data query are based on the search request that has been translated in to the database query language.

7. The method of claim 1, wherein performing the data query comprises:
identifying data within the at least one database corresponding to the union of the ontological dataset with the search keywords in the search request.

8. The method of claim 1, wherein returning the set of data to the user further comprises: sorting the set of data that has been returned to the user based on the grouping annotation associated with each data entry in the set of data.

9. An information processing system adapted to retrieving data from a database, the information processing system comprises:
a memory;
a processor communicatively coupled to the memory; and
a database manager communicatively coupled to the memory and the processor, wherein the database manager is configured to:
receive, from a user, a search request for a set of data in at least one database;
perform, in response to receiving the search request from the user, an ontology query over at least one ontology associated with at least one database resulting in an ontological dataset associated with the search request, wherein the ontological dataset comprises at least one of a set of synonyms, a set of hypernyms, and a set of hyponyms, associated with the search request;
perform, in response to performing the ontology query, a data query over data in the at least one database using a union of the ontological dataset with the search keywords in the search request;
provide to the user at least a portion of the set of data based on the data query that has been performed; and
dynamically adding a column to a table comprising the set of data in the at least one database, wherein each row in the column that has been added comprises a grouping annotation associated with a corresponding data entry in the set of data.

10. The information processing system of claim 9, wherein the search request received from the user comprises at least one of:
a set of search keywords;
a set of dimension specifications for at least one search keyword in the set of search keywords indicating whether the ontology query is to consider at least one of synonyms, hypernyms, and hyponyms in the at least one ontology associated with the at least one search keyword; and
an aggregation specification indicating at least one aggregation type for aggregating the at least one of synonyms, hypernyms, and hyponyms, in the at least one ontology for the at least one search keyword.

11. The information processing system of claim 9, wherein the database manager is further adapted to:
translate the search request received from the user into a database query language, wherein the ontology query and the data query are based on the search request that has been translated in to the database query language.

12. The information processing system of claim 9, wherein the database manager is further adapted to perform the data query by:
identifying data within the at least one database corresponding to the ontological dataset.

13. The information processing system of claim 9, wherein returning the set of data to the user further comprises:
sorting the set of data that has been returned to the user based on the grouping annotation associated with each data entry in the set of data.

14. A computer program storage product for retrieving data from a database, the computer program storage product comprising instructions for:
receiving, from a user, a search request comprising search keywords for a set of data in at least one database;
performing, in response to receiving the search request from the user, an ontology query over at least one ontology associated with at least one database resulting in an ontological dataset associated with the search request, wherein the ontological dataset comprises at least one of a set of synonyms, a set of hypernyms, and a set of hyponyms, associated with the search request;
performing, in response to performing the ontology query, a data query over data in the at least one database using a union of the ontological dataset with the search keywords in the search request, wherein performing the data query further comprises:
searching for a first set of data records associated with the search keywords; and
searching for a second set of data records associated with the ontological dataset; and
providing the set of data to the user based on the data query that has been performed searching for the first set of data records and the second set of data records, wherein returning the set of data to the user further comprises:
dynamically adding a column to a table comprising the set of data in the at least one database, wherein each row in the column that has been added comprises a grouping annotation associated with a corresponding data entry in the set of data.

15. The computer program storage product of claim 14, wherein the search request received from the user comprises at least one of:
a set of search keywords;
a set of dimension specifications for at least one search keyword in the set of search keywords indicating whether the ontology query is to consider at least one of synonyms, hypernyms, and hyponyms in the at least one ontology associated with the at least one search keyword; and
an aggregation specification indicating at least one aggregation type for aggregating the at least one of synonyms, hypernyms, and hyponyms in the at least one ontology for the at least one search keyword.

16. The computer program storage product of claim 14, further comprising instructions for:
storing the at least one ontology into the at least one database prior to performing the ontology query.

17. The computer program storage product of claim 14, further comprising instructions for:
translating the search request received from the user into a database query language, wherein the ontology query and the data query are based on the search request that has been translated in to the database query language.

* * * * *